United States Patent [19]
Cole

[11] Patent Number: 5,440,145
[45] Date of Patent: Aug. 8, 1995

[54] SAMPLING CHAMBER FOR A POLLUTION DETECTOR

[75] Inventor: Martin T. Cole, Keysborough, Australia

[73] Assignee: I.E.I. Pty. Ltd., Australia

[21] Appl. No.: 211,233

[22] PCT Filed: Oct. 14, 1992

[86] PCT No.: PCT/AU92/00546
§ 371 Date: Mar. 25, 1994
§ 102(e) Date: Mar. 25, 1994

[87] PCT Pub. No.: WO93/08461
PCT Pub. Date: Apr. 29, 1993

[30] Foreign Application Priority Data

Oct. 14, 1991 [AU] Australia .................. PK8877

[51] Int. Cl.6 .............. G01N 15/06; G01N 21/49
[52] U.S. Cl. ...................... 250/574; 356/336; 356/438; 250/237 R
[58] Field of Search .................. 250/237 R, 573, 574, 250/576, 222.2; 356/436–442, 336–343; 340/628, 630

[56] References Cited

U.S. PATENT DOCUMENTS

| | | |
|---|---|---|
| 3,417,392 | 12/1968 | Hansen et al. . |
| 3,874,795 | 4/1975 | Packham et al. ............ 250/574 |
| 3,976,891 | 8/1976 | Parkinson .................... 356/439 |
| 4,103,997 | 8/1978 | Araki et al. .................. 250/574 |
| 4,206,366 | 6/1980 | Marsocci et al. ............ 250/574 |
| 4,226,533 | 10/1980 | Snowman ..................... 356/338 |
| 4,242,673 | 12/1980 | Cooper ........................ 340/630 |
| 4,439,638 | 3/1984 | Dobrzanski .................. 250/381 |
| 4,607,915 | 8/1986 | Cole . |
| 4,665,311 | 5/1987 | Cole ............................. 250/574 |
| 4,672,217 | 6/1987 | Dobrzanski .................. 250/574 |
| 4,714,347 | 12/1987 | Cole ............................. 356/339 |
| 4,781,065 | 11/1988 | Cole ............................. 340/627 |
| 5,231,378 | 7/1993 | Dennis et al. ................ 250/574 |

FOREIGN PATENT DOCUMENTS

| | | |
|---|---|---|
| 573243 | 8/1984 | Australia . |
| 2016680 | 9/1979 | United Kingdom . |
| 2032617 | 5/1980 | United Kingdom . |
| 2034028 | 5/1980 | United Kingdom . |
| 2092820 | 8/1980 | United Kingdom . |

*Primary Examiner*—Stephone B. Allen
*Attorney, Agent, or Firm*—Learman & McCulloch

[57] ABSTRACT

A pollution/smoke detector apparatus is disclosed having a sample chamber of two part molded plastic construction having a pair of matching interlocking pairs including a series of interfitting baffles forming a series of irises spaced along the chamber, the apparatus including at one end a light receptor and a light absorber at the other end, and an air sample area between the subject of a flash light emitted from a light source module having a novel reflector element. The overall construction is easily assembled and disassembled for maintenance and yet provides effective and efficient operation.

8 Claims, 7 Drawing Sheets

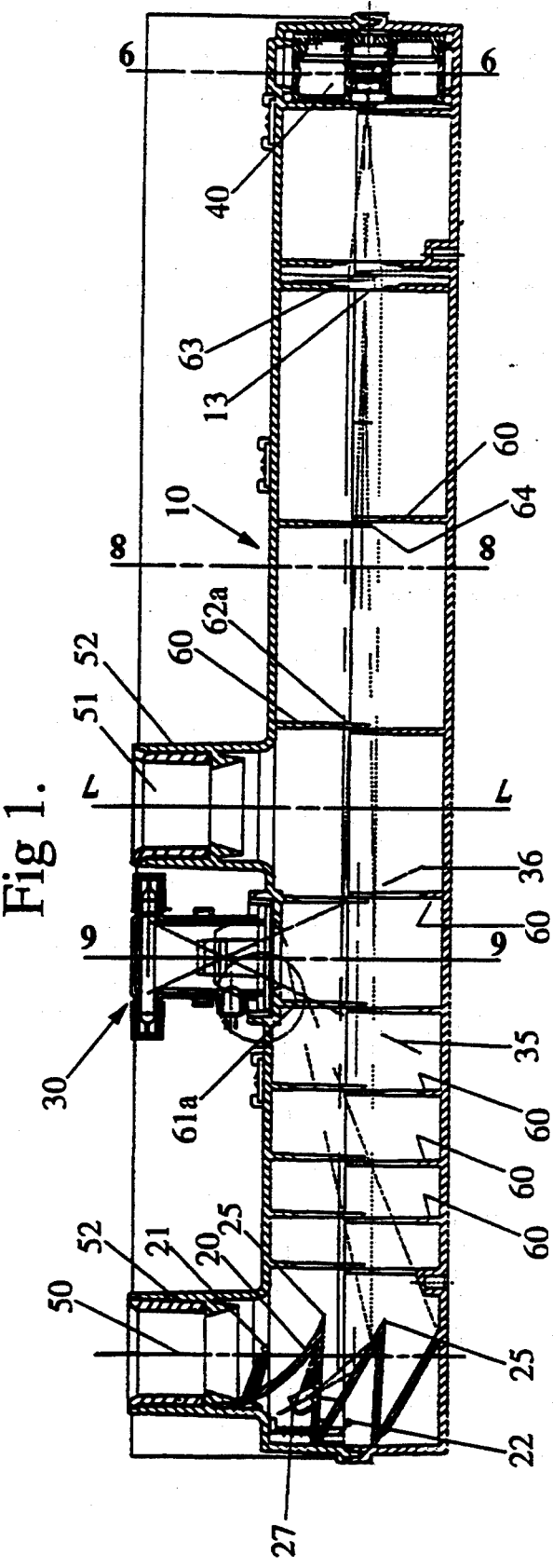

SAMPLING CHAMBER FOR A POLLUTION DETECTOR

This invention relates to construction of a sampling chamber for pollution detectors particularly smoke detectors and particularly to various aspects of the chamber construction including a light absorber module, a flashlight reflector module both mountable in the chamber and a modified chamber construction.

DESCRIPTION OF PRIOR ART

Previous work in this field has culminated in several US patents in my name including U.S. Pat. No. 4,714,347—Flash Reflector, U.S. Pat. No. 4,665,311—Smoke Detecting Apparatus, U.S. Pat. No. 4,607,915—Light Absorber and U.S. Pat. No. 4,781,065—Anemometer.

Prior art pollution detectors comprised a sampling chamber which included a cylindrical cavity in a metallic tube comprising some thirty assembled and manufactured parts to absorb light reflected off the internal walls off the tube and including coupling tubes for allowing air flow through the chamber. Between the coupling tubes a sealed reflector and window for a Xenon flash tube was positioned to irradiate any polluting particles entrained in the sample air within the chamber. The chamber at one end included an extremely sensitive light detector and a light absorber at the other end acting to prevent any stray reflected light being retransmitted to the light receiver. The sampling chamber 10 includes a series of irises spaced along the length of the chamber adapted to absorb and dissipate light reflected off the walls of the chamber. Coupling tubes are provided to circulate ambient air from an area under fire surveillance or pollution surveillance into the chamber into a region which is subject to light from the flash tube.

It is intended that light scattered from tiny fragments and molecules entrained in the sample air are directed along the length of the sample tube to impinge on the light receptor to give a reading of pollution in the sample air. Extreme accuracy has been obtainable with the detector of my previous patents and it is the objective of the present invention to further improve the efficiency and ease of construction of the sampling chamber and the various components therein.

The light sensing apparatus comprises a solid state photo cell responsive to low levels of light connected to an impedance matching buffer stage, a gain controlled amplifier stage and an output amplifier stage; a gain control network controlled by a temperature sensor for receiving an amplified signal from said output stage the gain being adjustable to compensate the temperature dependence of the photo cell signal.

The absorber as described in U.S. Pat. No. 4,607,915 includes a central light receiving conical surface inclined by at least one annular truncated conical surface to provide at least one annular groove or valley surrounding the central cone and wherein one wall of the groove or valley is optionally undercut to shade the base of the groove or valley from direct impinging light.

The U-shaped reflector described in U.S. Pat. No. 4,714,347 includes a concave reflecting element to focus light from each cross-sectional element of the arc of ionised gas in a flash tube, the light output from the whole length of the tube being focussed into the central region of the sampling chamber.

DESCRIPTION OF INVENTION

The present invention relates to three specific aspects of contemplated improvements as disclosed in the following specification.

Sample Chamber Construction

The sample chamber is essentially of a two part preferably moulded plastic construction having a pair of matching interlocking pairs and including as an integral part a series of spaced interlocking baffles forming a series of irises spaced therealong when the two interlocking pairs are connected together and in position. The chamber includes simple tongue and groove connections incorporating a rubber seal. A focussing lens is held in one of the apertures for focussing reflected light onto the light receptor. The lens is frictionally held between resilient fingers integrally formed in the chamber body.

The interior surfaces of the sampling chamber are finished in gloss black for the reason that any small amount (less than 2%) of light that is reflected from an internal surface is reflected in a known predictable direction, and is not scattered. Therefore any reflected light does not form any part of the pool of scattered light that may be generated in the sample area adjacent to the light source. In other words as near as practically the only scattered light generated in the sample chamber is that generated by the actual presence of particles in the sample area.

Furthermore, baffles with different sized apertures are located in spaced positions along the length of the chamber working to direct reflected light towards the walls of the chamber or beck towards the light absorber, but always directed away from the light receptor end of the chamber. The size of the apertures formed by the baffles in the vicinity of the light source are comparatively large compared with the size of the apertures in the baffles between the light receptor area and the sample area. Thus any stray reflected light tends to be reflected back towards the absorber end of the sample chamber which will be described in greater detail later.

Reflector

The reflector includes a partial elliptical cylinder adapted to house a straight line light source such as a Xenon flash tube with the reflector adapted to focus to the central axis of the chamber in a region located between a pair of aperture irises on each side of the light chamber. The reflector is constructed as a partial ellipse to ensure that only one reflection from the reflector plus unreflected light from the actual light tube is directed into the light chamber. The reflector construction is of modular form and is relatively simple to isolate and to seal against dirt and grime and makes lamp replacement and cleaning of the components relatively simple.

Testing of this reflector construction has shown that greater than 70% of light emitted from the light source is reflected into the light sampling area located in the sampling tube between the air intake and air outlet tubes provided to circulate ambient sampled air from areas under fire surveillance or pollution surveillance into the sample area of the sampling chamber. This compares favourably to the reflection disclosed in earlier referred to U.S. Pat. No. 4,714,347. Therefore the reflector construction of the present invention provides a high proportion of useable light for a given power light source thereby enabling as a practical matter reduction of power to the lamp, thereby resulting in power savings and lamp longevity.

The modular reflector is retained in the body of the sampling chamber in sealing relationship therewith by simple retaining clips enabling positive fixing but easy removal if necessary for maintenance purposes.

At a location adjacent to the light receptor sensing device at one end of the sample chamber, a focussing lens is located to focus received scattered light rays onto the light receptor which is described in greater detail in U.S. Pat. No. 4,665,311. The increased efficiency (mainly because of better control of stray light) of the chamber in accordance with this invention enables an increase in the aperture size of the focussing lens to at least double that used in previous detector apparatus and enabling a decrease in the required energy input to the Xenon lamp.

The baffles on each half of the sampling chamber cooperate to form apertures or irises of predetermined size along the length of the chamber and in the light path between the sample area and the light receptor. The edge of the baffles forming the apertures have a knife edge formation thereon to avoid any surface exposure to unwanted light beams which could be reflected onto the light receptor to create a false reading. The baffles have a tapered formation towards the ends so as to form an inclined face acting to reflect stray light back across the chamber toward the opposite walls rather than directly back to the absorber or receptor. The tapered formation of the baffle walls has the added benefit of enabling easy removal of the pans from the forming mould during manufacture thereof.

Absorber

The absorber includes a louvre-like construction including inclined surfaces reflecting light back into the valleys formed in the absorber. The peaks of the louvre construction and knife edge which form potential reflecting portions are strategically located well off the centre alignment of the chamber axis outside the vision area of the receptor as formed by the various irises spaced along the chamber. The absorber may include an LED calibration device for correction for variations in the absorbability of the absorber as the condition of the surface changes with age and consequent possible build up of grime.

The inclined surfaces overhang the valleys having a finite radius formed by the inclined surfaces to ensure that the valleys are shrouded from the receptor and prevent possible light reflection back to the receptor.

The calibration device may provide for periodic routine sensitivity checks of the apparatus and to correct for variation in signals caused by aging of the components including the lamp, the detector apparatus and any grime build up on the absorber surfaces and other interior surfaces of the chamber which will affect the reflectivity of the surfaces.

The calibration device is preferably a light emitting diode (LED) device which is operated as test device in substitution for the Xenon flash tube to simulate a light scatter proportional to a predetermined amount of smoke to be detected. Appropriate software in the microprocessor receiving signals from the light receptor is able to compare the signal received with a known reference signal and to recalibrate the device in accordance with any change in the received signal.

The absorber being located adjacent to the incoming sample air stream provides a good location for Zener diodes used in the anemometer or air movement indicator to provide a continuous indication of air flow thus ensuring that the monitor is sampling fresh batches of air from a monitored space. The Zener diode junction devices are located so that one is positioned in full exposure to the air flow coming into the sample chamber and the other junction device is located behind one of the inclined surfaces of the absorber but in a sheltered area where there is a reliable change of air ensured by good ventilation but without exposure to air flow. This ensures that there is no significant variation from ambient temperature in the air surrounding the sheltered Zener diode which would otherwise affect the accuracy and sensitivity of the air flow measurement device.

The invention will be described in greater detail with reference to the accompanying drawings.

DESCRIPTION OF THE DRAWINGS

FIG. 1 is a cross-sectional side view of the sampling chamber;

FIG. 2 is a cross-sectional plan view of the sampling chamber;

FIG. 6A is a partial enlarged sectional view of the retention clip;

DETAILED DESCRIPTION OF THE PRACTICAL EMBODIMENT

Sample Chamber Assembly

Figures 3, 3A, 3B:
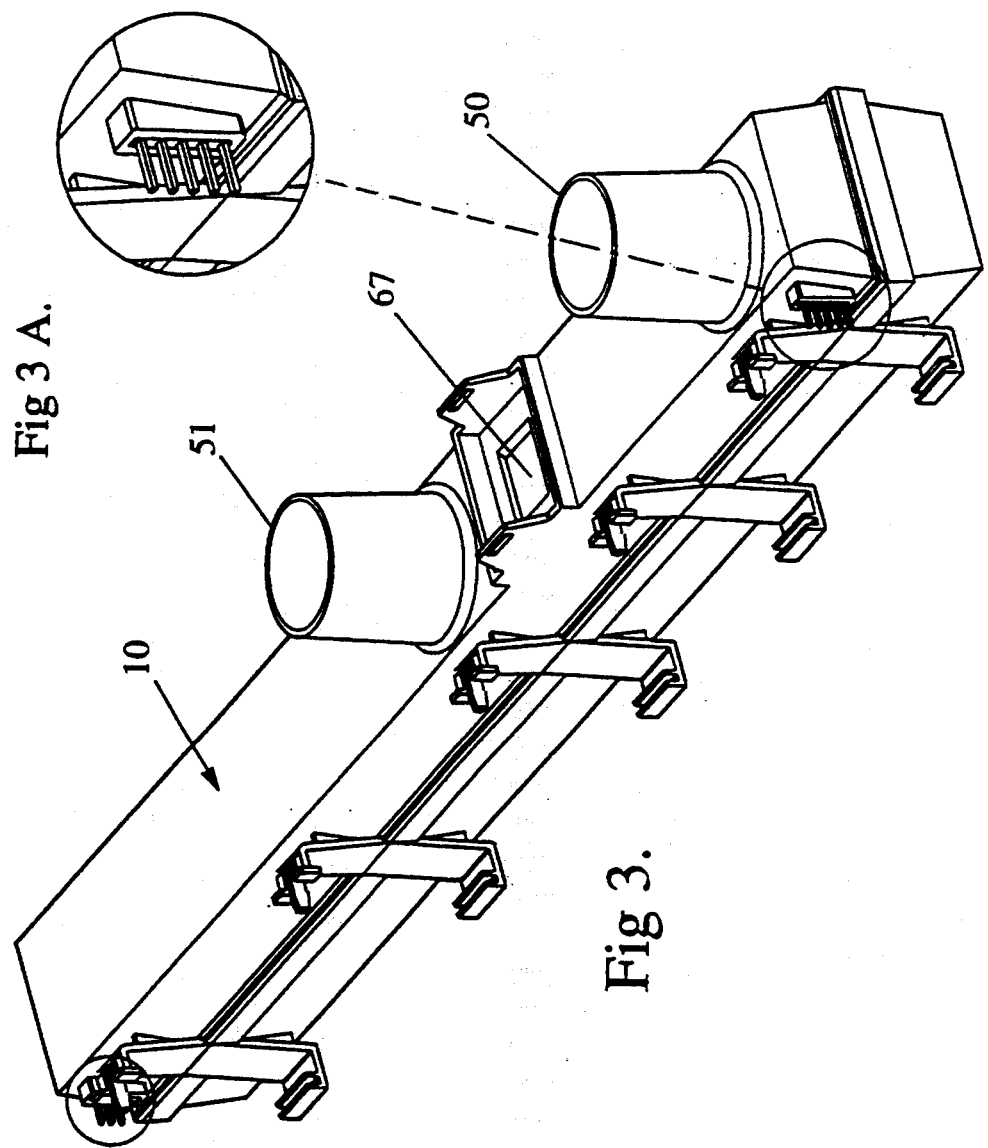
FIG. 3 is a perspective view from above of the sampling chamber.
FIGS. 3A and 3B are enlarged views of electrical plug connections.
Figure 5:
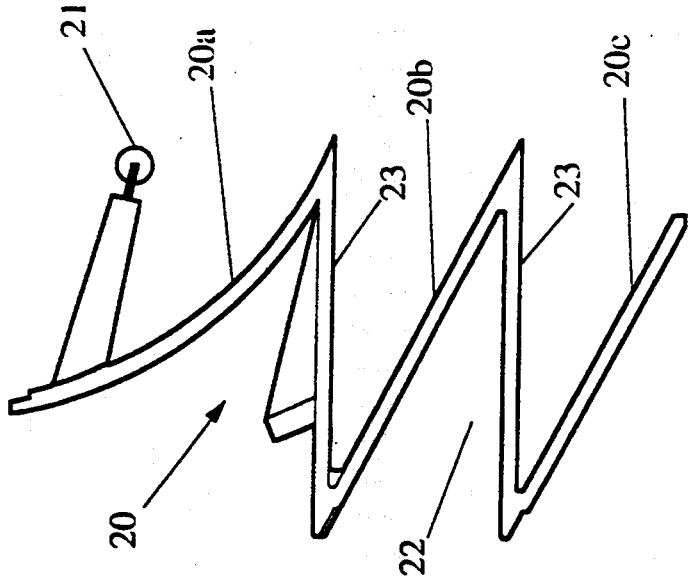
FIG. 5 is a side view of the absorber.
Figure 4:
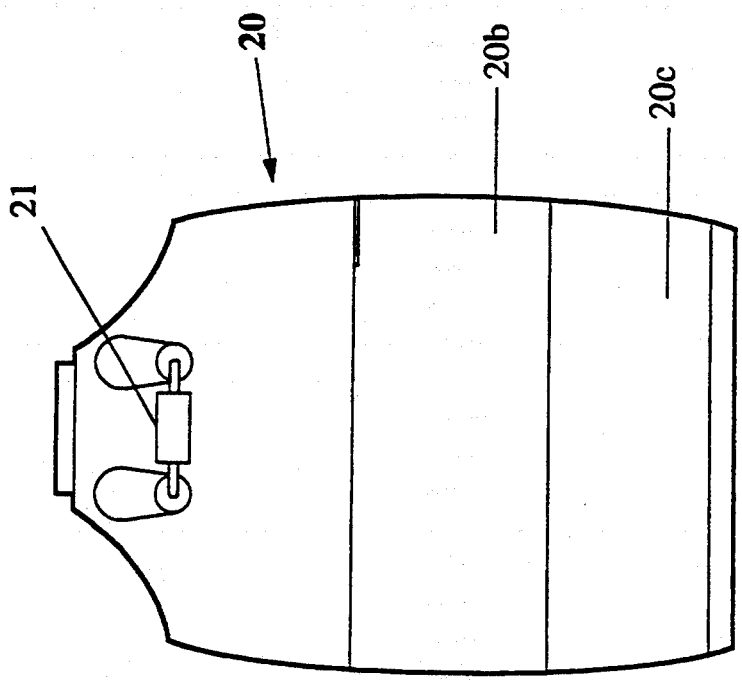
FIG. 4 is a front view of the absorber.
Figure 7:
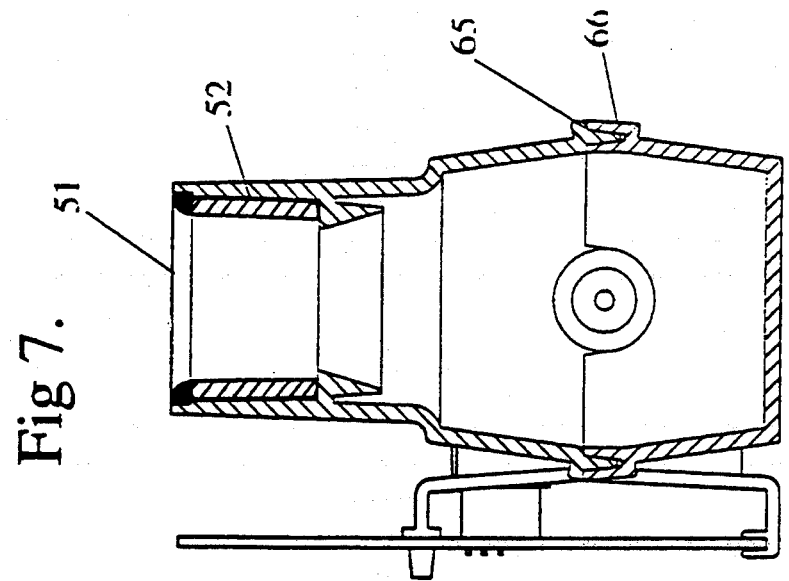
FIG. 7 is a cross-sectional view of the chamber sample air outlet taken on line 7—7 of FIG. 1.

The sample chamber assembly is comprised of an absorber 20, a light source module 30 and a light receptor 40 as shown in FIGS. 1 and 2. The chamber also includes inlet and outlet pipes 50,51 for allowing entry and exit of sample gas into the interior of the chamber. The pipes are fitted with resilient foam material 52 to receive in sealing relationship reticulation pipes used to carry air to and from the chamber from an area under surveillance for smoke or other like pollution.

Figure 10:
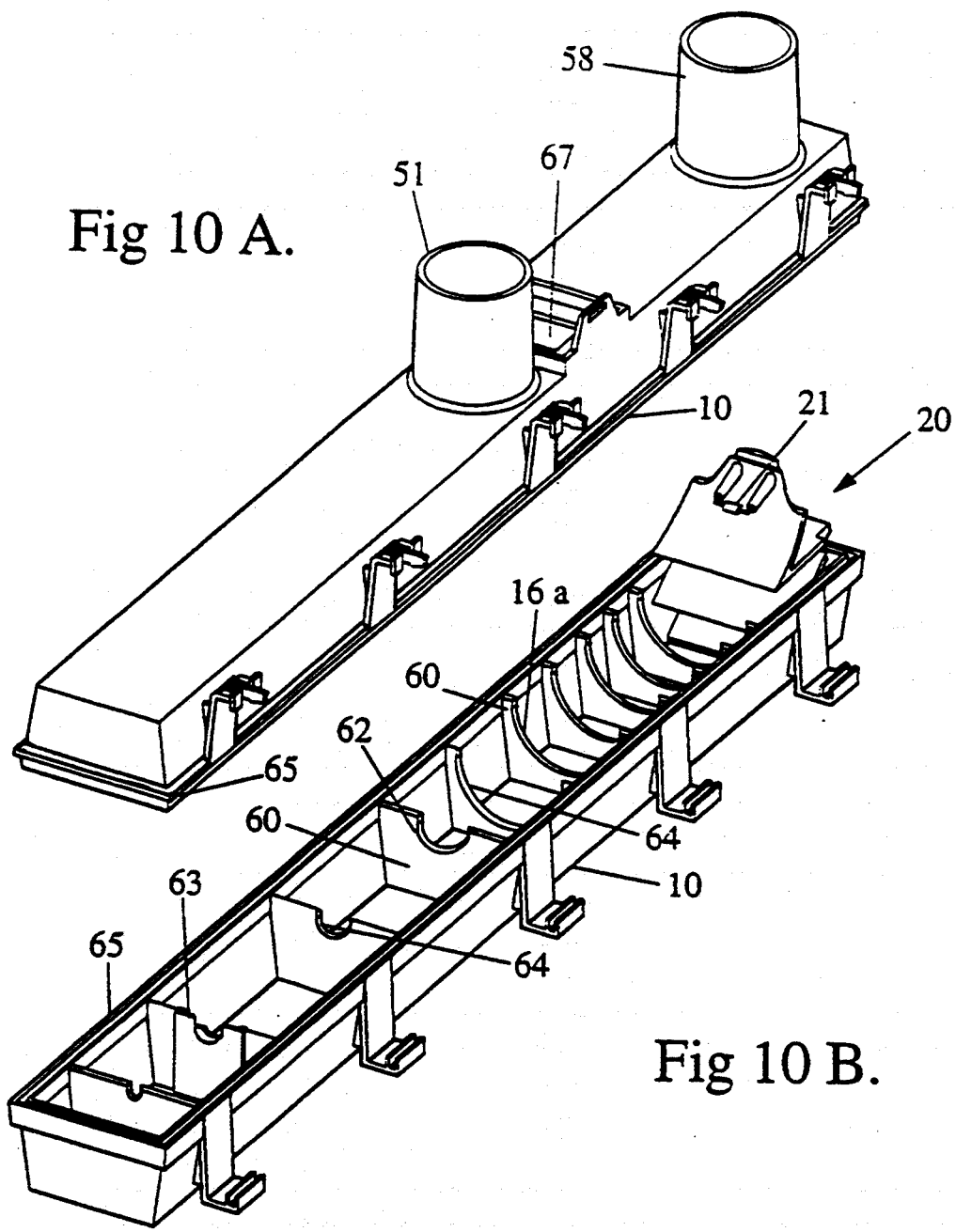
FIG. 10A is a plan perspective view of the top half of the sample chamber.
FIG. 10B is a plan perspective view of the bottom half of the sample chamber.
Figure 11:
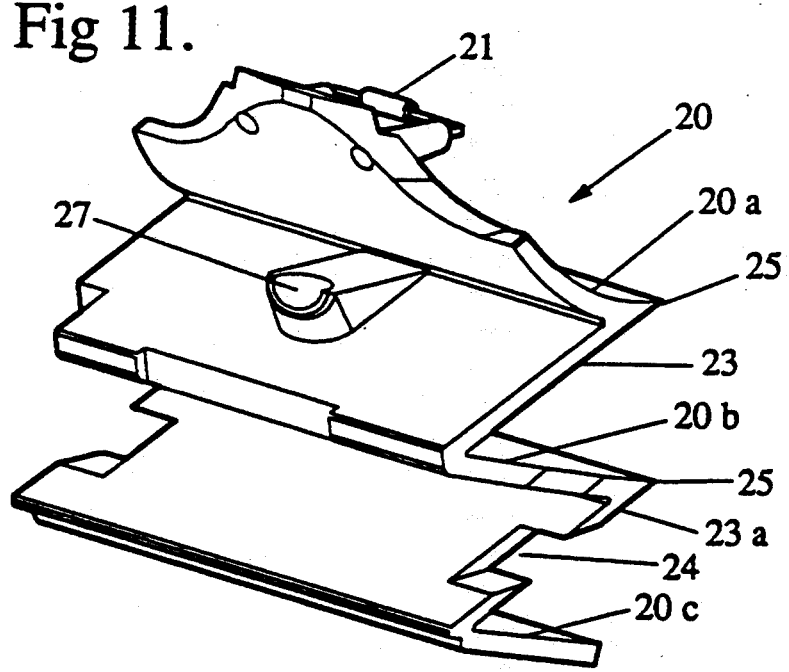
FIG. 11 is a perspective view of the rear of the light absorber.
Figure 12:
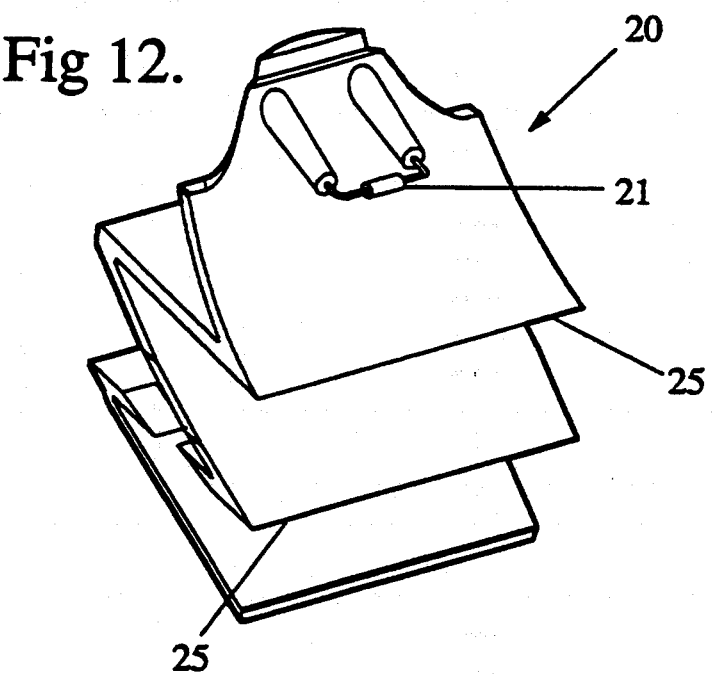
FIG. 12 is a perspective view of the front of the light absorber.

As is best shown in FIGS. 1 and 10B, the chamber includes a series of spaced baffles 60 in each half section including a central cut out portion arranged to form a circular centrally disposed aperture of varying diameter depending upon the location of the baffles relative to the light source area. It is essential that stray light reflections in the chamber not related to the detection of particles such as smoke are absorbed or do not impinge upon the light receptor or sensor 40.

The location and the configuration of the baffles 60 is important to ensure that scattered light created by the light beam emitted from the light source module 30 impinging upon particles in the gas stream flowing between pipes 50,51 is the only light that is allowed to reach the light receptor 40. Thus the aperture 61 and the baffles 60 in the gas sampling area between the pipes 50,51 are relatively large to allow free transmission of light back towards the absorber 20 and to reduce the surface area of the baffles facing towards the light receptor. By comparison the aperture 62 in the baffle 60 extending in the chamber away from the gas sample area towards the light receptor are relatively small, particularly aperture 62a.

Baffle 63 next adjacent to the light receptor 40 is of two part resilient construction to receive and locate a focussing lens 13 between the fingers of the two part baffle 63. The lens is fitted into one half of the sample chamber prior to assembly of the two parts of the chamber together. It is important that the size of the lens 13 is as large as possible (subject to adequate collection of stray light) to collect a large proportion of the scattered light impinging thereon which is then focussed onto the light receptor.

The baffles 60 are tapered inwardly towards their central axis so that any light impinging thereon will tend to be reflected back towards the opposite wall of the chamber. The taper also eases removal of the moulded part from its mould during manufacture. The edges of the apertures 64 are formed as knife edges to reduce to a minimum the surface area exposed to stray light reflections.

The baffle halves 60 on each half of the sample chamber are staggered as best shown in FIG. 1 to neatly interfit upon assembly of the two halves to form the apertures as described above. The two halves of the sample chamber include interconnectable tongue and groove sockets 65,66 extending continuously around the outer periphery of each chamber half as best shown in FIGS. 10A and 10B. The bottom of the groove is preferably fitted with a ring seal such as an O-ring seal for engaging the tongue when fitted therein to ensure effective hermetic sealing of the chamber against ingress of air, moisture and light.

Light Source and Reflector

Figure 6:
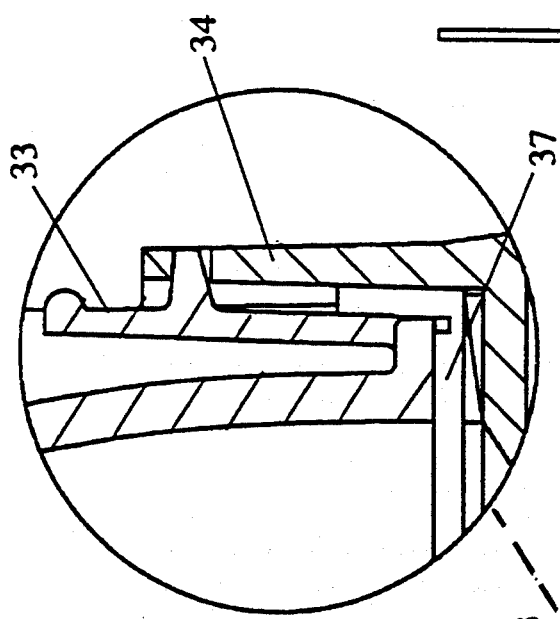
FIG. 6 is a cross-sectional view of the chamber lens module taken on line 6—6 of FIG. 1.
Figure 6:
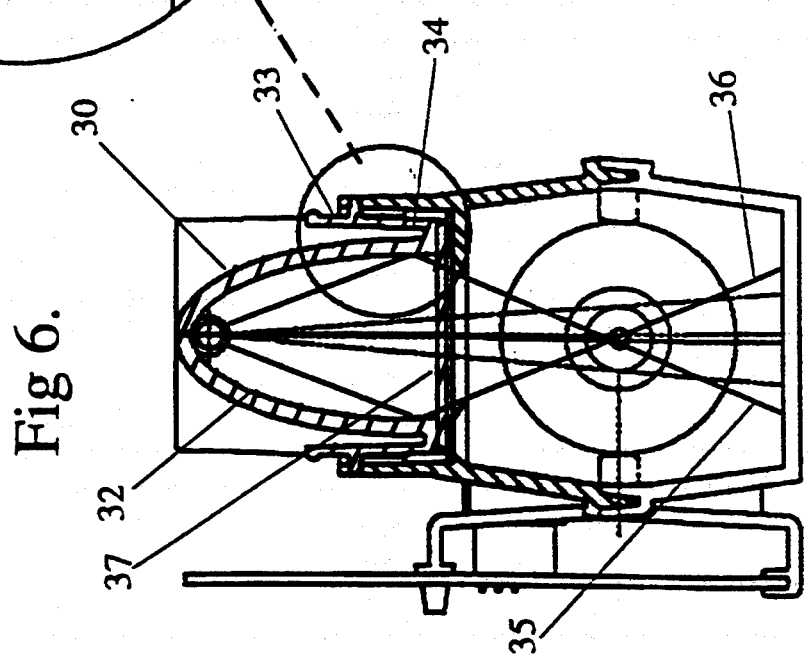
Figure 9:
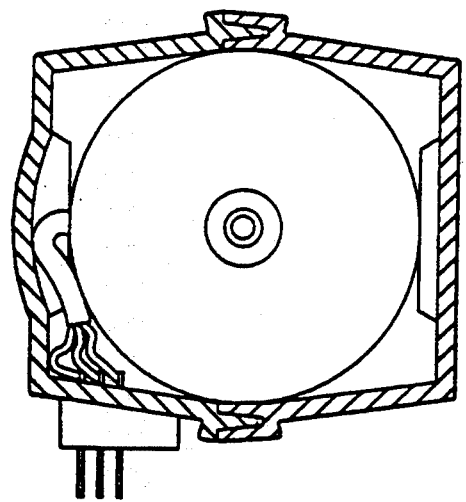
FIG. 9 is a cross-sectional view of the sample chamber light sensor taken on line 9—9 of FIG. 1.
Figure 8:
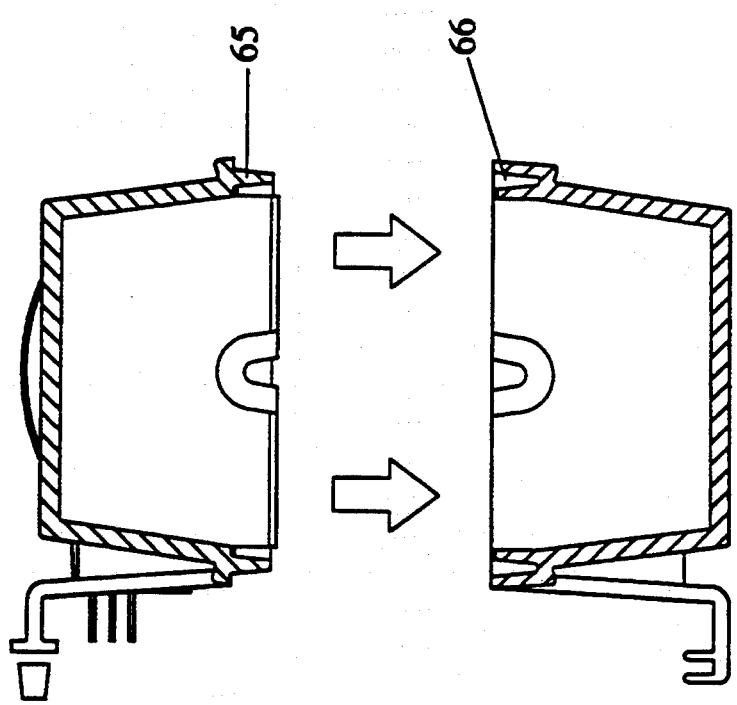
FIG. 8 is a view of the chamber which the two parts coming together on line 8—8 of FIG. 1.

The sample chamber includes a light source module 30 which includes a flash tube 31 which is preferably a straight Xenon gas flash tube, a reflector 32 configured as a partial elliptical cylinder surrounding the tube. The tube location and ellipse configuration is such that light emitted from the tube is reflected no more than once on the reflector surface before travelling into the space through which the sample air is passing between the inlet and outlet pipes 50,51. This minimises problems of alignment of the reflector relative to the sample volume and a less adverse affect on light brilliance. The reflector body 32 is removably and sealingly fitted to the sample chamber above an aperture 62 located between the inlet and outlet pipes 50,51. As best shown in FIGS. 6 and 6A, the base of the reflector body 32 includes spring clips 33 preferably formed as an integral part of the moulding for receipt in upstanding flanges 34 on the sample chamber top body half. Thus the reflector body is easily fitted and removed for maintenance and replacement of a light tube as required. The size of the aperture 67 is controlled so that light is restricted into the zone shown by lines of light 35,36 best shown in FIGS. 1 and 6.

The reflector body 32 can receive a clear panel 37 fitted in sealing relationship over the reflector opening and is particularly suitable for use in hazardous chemical locations where the light source must be hermetically sealed from the sample.

Optionally the reflector houses a light monitor device for the purpose of monitoring the intensity of the flash lamp, enabling the microprocessor to compensate for the flash to flash variation with light intensity of the flash lamp, or reduced light output of the lamp due to for example, aging of the lamp.

Absorber

With reference to FIGS. 1, 4, 5, 11 and 12 the device 20 is configured to absorb or deflect harmlessly any light impinging thereon away from the light receptor at the opposite end of the sample chamber. The light absorber includes sensing Zener diodes 21 and 22 with a diode 21 mounted with maximum exposure to incoming sample air through the inlet pipe 50 and diodes 22 located in a sheltered but well ventilated position between members 20, 23a of the absorber. Member 23a includes ventilation recesses 24 allowing circulation of air into the space but nevertheless protective the diode from direct exposure to the flowing air stream passing between the inlet and outlet pipes 50,51.

As previously mentioned the Zener diodes are part of the electronic circuit forming the anemometer described in the U.S. Pat. No. 4,781,065 hereby incorporated herein by cross reference.

The surface 20b is the surface directly in line of sight with the light receptor cell 40 and the condition of this surface and therefore any variation of reflectance of this surface is critical to the efficient operation of the apparatus. The absorber is preferably of black plastic material and particularly the same material that is used in the making of the other moulded components of the sample chamber. The surfaces 20, 20a, 20b and 20c are inclined at an angle to ensure any light impinging thereon is caused to reflect into the valleys of the absorber formed by the convergence of surfaces 20b and 20c with surfaces 23 and 23a and the lines of the valleys are shrouded by the inclined surfaces to prevent reflection of light back to the receptor.

The knife edges 25 across the absorber are located out of alignment with the light receptor so that there is no direct line reflection of light in central alignment with the various irises in each of the baffles extending along the chamber body. The absorber also houses a light emitting diode (LED) 27 with its light arranged to impinge upon surface 20b during instrument calibration checks described in greater detail later.

The absorber includes an LED 27 acting as a smoke level simulator as part of calibration circuit including the microprocessor receiving and interpreting signals received from the light receptor/sensor 40. In normal operation of the detector apparatus the microprocessor is programmed to receive signals from the light receptor 40 and to indicate whether particles exist in the sample area adjacent to the light source 30. This is evidenced by light striking such particles and being deflected in random manner as scattered light, some of which will be received by the light receptor 40. This in turn generates an electrical signal which is transmitted to the microprocessor and interpreted thereby.

In normal operation the device requires calibration to take account of practical variations in the intensity of the light source, the reflectance of the absorber and other factors. The LED 27 acts as a smoke level indicator of known intensity with a microprocessor programmed to receive the signal generated by the LED light impinging upon the light receptor. Thus the microprocessor readily checks the signal against a reference signal for the detector and automatically recalibrates the detector to correct for any variations that may have occurred as caused by dirt build up on internal surfaces, variation in lamp intensity and the like.

As is best shown in FIGS. 3, 3A and 3B there are provided fittings on the side of the sample chamber as assembled which allow easy attachment to sideboards and standard electrical connections as shown in FIGS. 3A and 3B are provided for connection to the anemometer apparatus, the calibration apparatus and the light receptor apparatus.

The claims defining the invention are as follows:

1. In a pollution detection apparatus comprising a sample chamber having a flashing light source of predetermined light intensity for irradiating light rays into a specific volume of the chamber, fluid inlet and outlet means for passing fluids being surveyed into said specific volume so that the fluid travels across the path of said light rays, the arrangement being such that a particle struck by the light rays will cause random reflection and scattering of said rays, a light receptor device positioned in the chamber to receive at least some of said scattered rays to provide a signal indicating the extent of light scattering and therefore pollution existing in the sample, the improvement wherein the chamber is of two separable interfitting pans including a series of spaced apertured baffles forming, when the parts are assembled, a series of aligned apertures between the specific volume and the light receptor acting to prevent transmission of unscattered light onto the light receptor.

2. The apparatus as claimed in claim 1 wherein one of the baffles houses a lens for focussing light onto said light receptor.

3. The apparatus as claimed in claim 1 or 2 wherein the lens baffle includes resilient finger means for removably fixing the lens in alignment with the light receptor.

4. A reflector for a light source for a pollution detection apparatus, said apparatus comprising a sample chamber having a flashing light source of predetermined light intensity for irradiating light rays into a specific volume of the chamber, fluid inlet and outlet means for passing fluid being surveyed into said specific volumes so that the fluid travels across the path of said light rays, the arrangement being such that a particle or particles in the fluid struck by the light rays will cause random reflection and scattering of said rays, a light receptor device positioned in the chamber to receive at least some of said scattered rays to provide a signal indicating the extent of light scattering and therefore pollution existing in the sample, said reflector including a partial elliptical cylinder configuration adapted to house a light source such as a Xenon flash tube, the reflector being adapted to focus light at a central region of the specified volume in the sample chamber, the arrangement being such that no more than one reflection of the light beam occurs in reaching said point of focus.

5. A reflector for a light source as claimed in claim 4 wherein the reflector and light source is constructed as a module, fastening means for releasably and sealingly securing said module to said sample chamber.

6. An absorber for a light source for a pollution detection apparatus, said apparatus comprising a sample chamber having a flashing light source of predetermined light intensity for irradiating light rays into a specific volume of the chamber, fluid inlet and outlet means for passing fluid being surveyed into said specific volumes so that the fluid travels across the path of said light rays the arrangement being such that a particle or particles in the fluid struck by the light rays will cause random reflection and scattering of said rays, a light receptor device positioned in the chamber to receive at least some of said scattered rays to provide a signal indicating the extent of light scattering and therefore pollution existing in the sample, said absorber including a louvered construction having inclined surfaces extending across the end of said sample chamber opposite to said light receptor, the inclination of said surfaces being such that impinging light is reflected back into valleys formed by the inclined surfaces of the absorber.

7. An absorber as claimed in claim 6 wherein at least two inclined surfaces are provided and connected in a zig zag configuration forming the light receiving surfaces, the surfaces acting to shroud the lines formed by the said valleys and avoiding reflection of light onto the light receptor.

8. In a pollution detector apparatus comprising a sample chamber having a flashing light source of predetermined light intensity for irradiating light rays into a specific volume of the chamber, fluid inlet and outlet means for passing fluids being surveyed into said specific volume so that the fluid travels across the path of said light rays, the arrangement being such that a particle struck by the light rays will cause random reflection and scattering of said rays, a light receptor device positioned in the chamber to receive at least some of said scattered rays to provide a signal indicating the extent of light scattering and therefore pollution existing in the sample, the improvement wherein an LED calibration device is arranged within the chamber for correction of variations in light reflection within the chamber caused by surface ageing and grime build up, said calibration device acting to substitute in test mode for the flash light to simulate light scatter proportional to a predetermined amount of smoke or like pollution, a microprocessor receiving signals from the light receptor in said test mode to compare the signal with a known reference signal and acting to recalibrate the apparatus in accordance with any change in the received signal.

* * * * *

UNITED STATES PATENT AND TRADEMARK OFFICE
CERTIFICATE OF CORRECTION

PATENT NO. : 5,440,145
DATED      : August 8, 1995
INVENTOR(S): Martin T. Cole

It is certified that error appears in the above-identified patent and that said Letters Patent is hereby corrected as shown below:

Column 2, line 36, change "beck" to -- back --.

Column 3, line 35, change "pans" to -- parts --.

Column 7, line 37, change "pans" to -- parts --.

Signed and Sealed this

Thirty-first Day of October 1995

Attest:

BRUCE LEHMAN

*Attesting Officer*          *Commissioner of Patents and Trademarks*